United States Patent
Koshti et al.

(10) Patent No.: US 6,426,435 B1
(45) Date of Patent: Jul. 30, 2002

(54) SUBSTANTIVE WATER-SOLUBLE BIS-QUATERNARY SALTS OF CINNAMIDOALKYLAMINES

(75) Inventors: Nirmal Madhukar Koshti; Arun Harchandra Jawale; Bharat Bhikaji Parab; Shubhangi Dattaram Naik; Manasi Dattatraya Moghe; Tanaji Shamrao Jadhav; Subhash Shivling Nashte, all of Maharashtra (IN)

(73) Assignee: Galaxy Surfactants Ltd., Maharashtra (IN)

( * ) Notice: Subject to any disclaimer, the term of this patent is extended or adjusted under 35 U.S.C. 154(b) by 0 days.

(21) Appl. No.: 09/917,953

(22) Filed: Jul. 31, 2001

(30) Foreign Application Priority Data

Oct. 6, 2000 (IN) .................................... 904/MUM/2000
Oct. 6, 2000 (IN) .................................... 903/MUM/2000

(51) Int. Cl.$^7$ .......................... C07C 233/09; A61K 7/42
(52) U.S. Cl. ....................... 564/157; 564/134; 564/142; 564/154; 514/618; 514/619; 514/620; 424/59; 424/401; 424/701; 424/709
(58) Field of Search ................................ 564/157, 154, 564/162, 163, 166, 182, 170, 134, 142; 424/709, 701, 401, 59; 514/618, 619, 620

(56) References Cited

U.S. PATENT DOCUMENTS 5,117,058 A * 5/1992 Chen et al. .................. 564/157
5,633,403 A * 5/1997 Gallagher et al. .......... 564/157

* cited by examiner

Primary Examiner—Shailendra Kumar
(74) Attorney, Agent, or Firm—Birch, Stewart, Kolasch & Birch, LLP

(57) ABSTRACT

Substantive UV-absorbing water-soluble quaternary salts of cinnamidoalkylamine of formula I. Hair, skin and fabric care compositions containing the compounds of formula I;

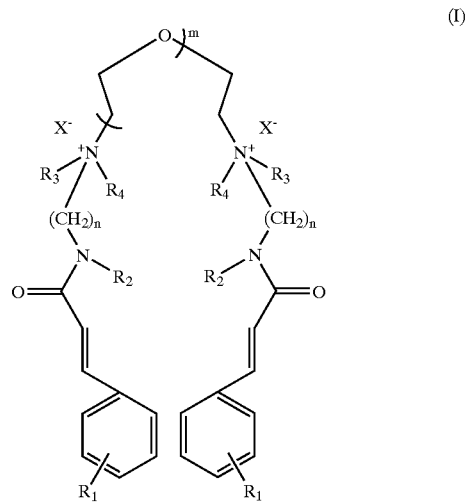

wherein $R_1$ represents up to four substituents, same or different, selected from H, halo, —OH, —NH$_2$, —NO$_2$, —OCH$_3$, —N(CH$_3$)$_2$, alkyl groups containing up to 6 carbon atoms, alkoxy groups containing up to 6 carbon atoms, alkylamino or N,N-dialkylamino groups containing up to 6 carbon atoms; $R_2$ is selected from hydrogen, alkyl group containing up to 6 carbon atoms; $R_3$ and $R_4$ are independently selected from benzyl, alkyl group containing up to 6 carbon atoms; n is an integer from 1 to 6; m is an integer from 1 to 10; X$^-$ is a counter anion of quaternary centres selected from halides including chloride, bromide, iodide and methane sulphonate and its derivatives such as trifluoro methane sulphonate, benzene sulphonates including its p-bromo, nitro and methyl derivative.

15 Claims, No Drawings

SUBSTANTIVE WATER-SOLUBLE BIS-QUATERNARY SALTS OF CINNAMIDOALKYLAMINES

FIELD OF INVENTION

The invention relates to substantive water-soluble bis-quatemary salts of cinnamidoalkylamines. More particularly, the invention relates to novel, cationic, non-hydrolysable, non-irritating UV-absorbing bis-quaternary salts of cinnamidoalkylamines which are substantive to fabric, skin and hair. The invention also relates to a process of manufacture of the said compounds and further to their use in hair, skin and fabric care formulations.

BACKGROUND AND PRIOR ART

The harmful effects of solar UV-radiation on skin are well known. The UV-B (290–320 nm) portion of solar spectrum is largely responsible for erythema (sunburn) and cancer. [M. M. Rieger, Cosmet. Toiletries, 102 (3), 91, (1987); L. Taylor, Skin Cancer Foundation J., 4, (90) (1986)].

Similarly, photodegradative effect of UV-radiation on human hair is well documented. Continuous exposure to sunrays makes human hair color and makes human hair rough, brittle and difficult to comb. UV rays are reported to damage the proteins of cuticles. Prolonged irradiation results in diminished tensile strength due to breaking of disulphide bonds in keratin, [R. Beyak et al, J. Soc. Cosmet. Chem. 22, 667–668 (1971), E. Hoting et al, J. Soc. Cosmet. Chem. 46, 85–99 (1995)].

In addition, UV light is also known to fade garments. [P. C. Screws, Text. Chem. Color, 11, 21 (1987); B. Milligan et al, Polym. Degrad. Stab. 10 (4), 335 (1985)].

A number of UV-absorbing compounds like derivatives of salicylic acid, benzophenones, benzotriazoles, cinnamic acid have been used in personal care products. However, all these molecules suffered from a major disadvantage of lack of substantivity. To make this UV-absorbing moieties more substantive, structural modification have been introduced.

U.S. Pat. No. 5,601,811 (1997) describes substantive UV-absorbing quaternary ammonium compounds containing cinnamidoalkylamine and product compositions for detergents, household cleaners and hair and skin personal care products. However, these products are said to be either water-soluble or water-dispersible. Bis-quaternary compounds of U.S. Pat. No. 4,734,277 (1988) are synthesised from cinnamidoalkylamine and alkylchlorohydrin forming a linker of an alkyl group with a hydroxyl group beta to one of the quaternary nitrogens, thus giving an unsymmetrical bis-quaternary molecule.

The main object of the present invention is therefore to synthesise highly water-soluble molecules containing cinnamido moiety to provide UV absorption and with cationic centre to provide substantivity to skin, hair and fabric.

The inventors have found that symmetrical bifunctional quaternising agents with oxyethylene linkage in the synthesis of UV-absorbing bis-quaterneries boosts hydrophilicity. High water solubility is desirable because these kind of substantive compounds can be formulated in oil-free compositions so that greasy feel of cosmetic preparations based on hydrophobic carrier can be avoided. Due to their substantive nature constant reapplication of the sunscreen preparation is not necessary in activity like swimming. Hence, the compounds of the present invention are designed to address the need for highly water-soluble yet substantially substantive sunscreen molecules.

SUMMARY OF THE INVENTION

Thus the present invention provides novel, substantive, water-soluble bis-cinnamidoalkylamine quaternary compounds of Formula I,

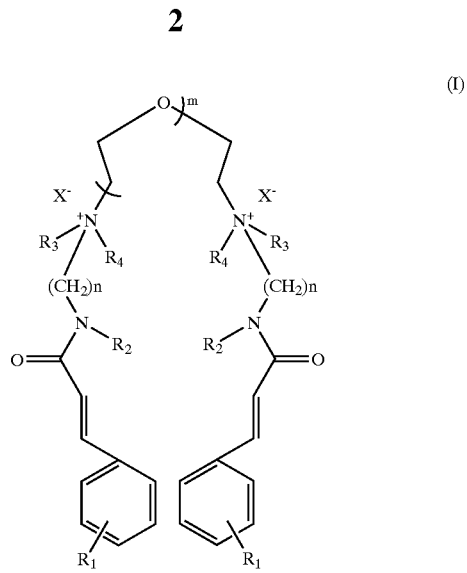

wherein $R_1$ represents up to four substituents, same or different, selected from H, halo, —OH, —NH$_2$, —NO$_2$, —OCH$_3$, —N(CH$_3$)$_2$, alkyl groups containing up to 6 carbon atoms, alkoxy groups containing up to 6 carbon atoms, alkylamino or N,N-dialkylamino groups containing up to 6 carbon atoms;

$R_2$ is selected from hydrogen, alkyl group containing up to 6 carbon atoms;

$R_3$ and $R_4$ are independently selected from benzyl, alkyl group containing up to 6 carbon atoms;

n is an integer from 1 to 6; m is an integer from 1 to 10;

$X^-$ is a counter anion of quaternary centres selected from halides including chloride, bromide, iodide and methane sulphonate and its derivatives such as trifluoro methane sulphonate, benzene sulphonates including its p-bromo, nitro and methyl derivatives.

The invention further relates to a process of making a water-soluble quaternary ammonium salt of bis-cinnamidoalkylamine of Formula I

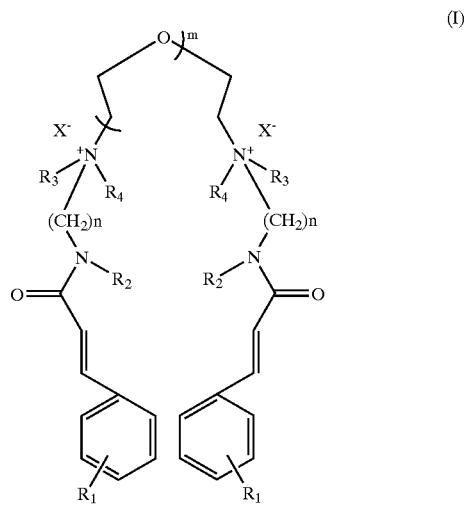

wherein R₁ represents up to four substituents, same or different, selected from H, halo, —OH, —NH₂, —NO₂, —OCH₃, —N(CH₃)₂, alkyl groups containing up to 6 carbon atoms, alkoxy groups containing up to 6 carbon atoms, alkylamino or N,N-dialkylamino groups containing up to 6 carbon atoms;

R₂ is selected from hydrogen, alkyl group containing up to 6 carbon atoms;

R₃ and R₄ are independently selected from benzyl, alkyl group containing up to 6 carbon atoms;

n is an integer from 1 to 6; m is an integer from 1 to 10;

—X⁻ is a counter anion of quaternary centres selected from halides including chloride, bromide, iodide and methane sulphonate and its derivatives such as trifluoro methane sulphonate, benzene sulphonates including its p-bromo, nitro and methyl derivative;

wherein, a compound of Formula II is first reacted with a compound of Formula III and the intermediate of Formula IV thus obtained is quaternised with a compound of Formula V,

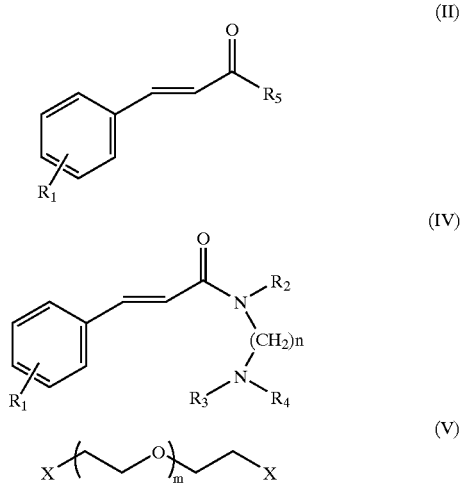

wherein in all these Formulae, R₁, R₂, R₃, R₄, m, n and X⁻ have the same meaning as Formula I and R₅ of Formula II is selected form —OH, Cl⁻ or —O(CH₂)$_p$CH₃ with p=0 to 3.

In another aspect this invention provides compositions containing quaternary ammonium compounds that are water-soluble, UV-absorbing and substantive to skin, hair and textile fibres. The unique combination of substantivity to hair and skin, strong UV absorption and water-solubility of these quaternary compounds of bis-cinnamidoalkylamines is very desirable for personal care products, especially for skin care applications.

DETAILED DESCRIPTION OF THE INVENTION

The UV absorbing compounds of the present invention are quaternary salts of cinnamidoalkylamines that are prepared by reacting lower alkyl ester of cinnamic acid or acid halides of cinnamic acid with an amino compound that is subsequently quaternised with bifunctional alkylating agents.

In the process, the amidification reaction between a compound of the Formula II when R₅=—OH or —O(CH₂)$_p$CH₃ (p=0 to 3), with that of Formula III is carried out at from about 120° C. to about 200° C., under pressure from about 10 psi to about 100 psi, in the presence of a basic catalyst such as sodium methoxide, sodium hydroxide from 0.25% to 5.0% by weight of the reaction mass, to afford the intermediate compound of Formula IV.

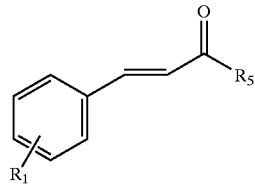

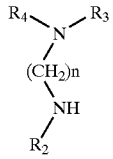

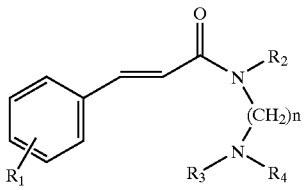

Preferred amount of such catalyst is 1.0% w/w of total reaction mass. The reaction is conveniently monitored by TLC or HPLC using UV detection. After the complete disappearance of cinnamic acid ester, the excess diamine is distilled off under vacuum.

Alternately, this reaction is carried out in the presence of a basic catalyst such as sodium methoxide, sodium hydroxide from 0.25% to 5.0% by weight of the reaction mass under atmospheric pressure, under blanket of nitrogen, with an arrangement for continuous selective removal of lower alcohol formed in the reaction.

Thus, the condensation reaction of one mole of cinnamic acid ester is carried with 1.0 to 3.0 moles of diamine at 120 to 200° C., preferably at 180° C., for 12 to 36 hours. The amines themselves can catalyse the reaction, however, the rates are found to be slower as compared with the bases like sodium methoxide and the like.

The same reaction can be performed using cinnamic acid in place of cinnamic acid ester at temperatures up to 200° C. and pressures of 100 psi, keeping the same stoichiometry (1:1.0 to 3). The excess diamine serves as solvent for the reaction.

Cinnamic acid esters and amino compounds are selected that are liquid within the disclosed temperature and pressure range.

The amidification reaction between a compound of Formula II when R₅=—Cl in the presence of a solvent, is carried out with that of Formula III at room temperature in the presence of solvent. The compounds of Formula IV are synthesised by reacting acid chlorides of Formula II (1.0 mole) when R₅ is —Cl with the diamines of Formula III (1.0 to 1.2 mole) at 20–50° C. in an inert solvent like dichloromethane, ethylene dichloride, tetrahydrofuran and the like.

In the process the cinnamidoalkylamines (Formula IV, I mole) are N-alkylated with bifunctional quaternising agents (Formula V, 0.5 mole, wherein, X⁻ is same as in Formula I)

in the presence of a suitable inert solvent that governs the temperature at which the reaction is carried out.

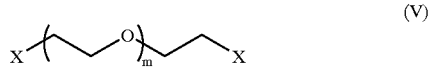

(V)

Quaternization of cinnamidoamines is carried out in the inert solvents that include lower alkanols, glycols, water and combinations thereof. Lower alkanols having one to four carbons atoms are suitable for use with the present invention. Glycols having from three to eight carbon atoms are suitable for use with the present invention. However, water is the most suitable solvent. The inert solvents are present in the reaction mass to extent of 20 to 80% resulting in solids content of final product from 80 to 20%.

The quaternisation reaction can be conveniently done in a pressure reactor as well as in an open system. The temperatures suitable for pressure reaction range from about 60–120° C. with the pressures up to 50 psi. The pressures are governed by the amount of solvent and the temperature selected for the reaction. The conditions of reaction in an open vessel also get dictated by the choice of solvent. The reactions are usually carried out at boiling point or slightly below boiling point of the solvent employed. The resulting bis-quaternary salts are obtained as concentrated solutions in either water, or an inert solvent. The progress of the reaction is monitored by measuring the amount of unreacted alkylating agent by chromatography or by estimation of unquaternized amidoamine or by estimation of $X^-$.

On quaternizatteon, the alcoholic solvents or water can be easily removed from concentrated solutions of quaternary ammonium salts to obtain solvent free pure compounds. However, they are slightly tacky, hygroscopic solids and difficult to handle. Hence, it is convenient to market or use these products as concentrated solutions.

Since most of the quaternizations are conveniently carried out in aqueous medium, the bis-quaternaries of the present invention may be marketed in this form for many end-use applications such as hair care, skin care and fabric care compositions.

The UV-absorbing compounds of the present invention are bis-quaternary salts of cinnamic acid amido amines. The cinnamic acid amido amines are prepared by reacting lower alkyl esters of cinnamic acid with an amino compound having a second tertiary amino group that is subsequently quaternized. Thus, the precursors of the present invention include essentially any quaternizable reaction product of lower alkyl ester of cinnamic acid and amino compound having a second tertiary amino group, provided that both the reactants are not very hydrophobic so that on quaternizing, the quaternary compounds formed are not rendered water-insoluble.

The compounds of the present invention include bis-quaternary amidoamine linked through oxyethylene bridge between the two quaternary centres. The object of this invention is to obtain UV absorption through cinnamido moiety, significant levels of substantivity through two cationic centres and finally excellent water solubility from the cationic centres as well as oxyethylene chain between the two quaternary centres.

The number and their nature of selected substituents should not be too hydrophobic to render the final bis-quaternary water-insoluble. For purposes of the present application, water-soluble compounds are defined as being soluble in water at levels above 15% w/w. These water-soluble compounds of this invention are useful for making compositions for skin and hair care and fabric care.

The preferred bis-quaternary compounds in accordance with the present invention form aqueous solutions at levels of at least about 15% by weight. The more preferred quaternary compounds in accordance with the present invention have a solubility of at least about 25% by weight. The most preferred compounds have a water-solubility of at least 50% w/w.

The bis-quaternary ammonium compounds in accordance with the present invention have the structure of Formula I.

As shown in Formula I, the benzene ring preferably contains one substituent at para position, $R_1$ is selected from moieties such as halo, p-OH, $-NH_2$, $-NO_2$, $-OCH_3$, $-N(CH_3)_2$.

Referring again to Formula I, the amido nitrogen is preferably is either unsubstituted ($R_2$ is hydrogen) or may contain a substituent, selected from alkyl groups containing up to 6 carbon atoms.

The quaternized nitrogen of the compounds in accordance with the present invention preferably contains two substituents, $R_3$ and $R_4$, as depicted in Formula I, $R_3$ and $R_4$ are independently selected from hydrogen, benzyl and alkyl groups containing up to 6 carbon atoms.

The compounds of the present invention are bis-quaternary salts of cinnamidoalkylamines as shown in Formula I, in which n is an integer between 1 and 6, both inclusive. Preferred compounds in accordance with the present invention are bis-quaternary salts of cinnamidoalkylamines in which n is an integer between 2 and 6, both inclusive and most preferably, n of Formula I is 3.

The compounds of the present invention are bis-quaternary salts of cinnamidoalkylamines as shown in Formula I, in which m is an integer between 1 to 10, both inclusive. The preferred value for m is between 2 to 6.

The bis-quaternary salts of the present invention are formed from bifunctional alkylating agent and its homologues where m is an integer between 2 and 6, both inclusive (Formula V). It is well understood by those with ordinary skill in the art, that the bis-quaternary salts of the present invention, will also include an anion derived from quaternisation reactions. Given the quaternizing agents described above, the quaternary salts of the present invention will contain an anion, such as $X^-$ of Formula I, selected from chloride, bromide, iodide, sulphate, alkosulphate, mesylate, triflate, tosylate and the like.

In another embodiment the process of the present invention relates to manufacture of a compound of Formula I, namely, β, β'-di(p-methoxy cinnamidopropyldimethyl ammonium chloride)ethyl ether, when $R_1=-OCH_3$, $R_2=H$, $R_3=R_4=-CH_3$, $X^-=Cl^-$, m=1 and n=3, from the compounds of Formula II, namely, p-methoxy ethyl cinnamate), and Formula III, namely, N,N-dimethylpropyldiamine, to form an intermediate compound of Formula IV, namely, p-methoxy cinnamidopropyldimethyl amine and Formula V, namely, bis-2-chloroethyl ether, with respective substituents $R_1$ of Formula II, $R_2$, $R_3$, $R_4$ and n of Formula III and $X^-$ and m of Formula V as defined for the compounds of Formula I in this embodiment, and $R_5$ of Formula II being ethoxy.

Cinnamidoalkylamine (Formula IV) are in turn synthesized by amidification of lower alkyl esters of cinnamic acid (Formula II, alkoxy group ($R_5$) may vary from $C_1$ to $C_4$) by appropriate diamines (Formula III) containing a tertiary amino group. $R_1$, $R_2$, $R_3$ and $R_4$ of cinnamidoalkylamine (Formula IV) and the diamine (Formula III) are the same as described with respect to Formula I.

The amidification reaction is performed at temperatures up to 200° C. and pressures up to 100 psi. Accordingly, cinnamic acid esters and amino compounds are selected that are liquid within the disclosed temperature and pressure range. This reaction generates lower alcohol that need not be distilled out.

In the present invention the reaction of one mole of cinnamic acid ester is carried with 1.2 to 3 moles of diamine at 130 to 200° C., preferably at 180° C., for 12 to 36 hours. This condensation is catalysed by bases such as sodium hydroxide, sodium methoxide or ethoxide, potassium hydroxide and the like. The amines themselves can catalyse the reaction, however, the rates are found to be slower as compared with the bases like sodium methoxide and the like.

From about 0.5% to 5.0% w/w of the basic catalyst should be employed. Preferred amount of such catalyst is 1.0% w/w. The reaction is conveniently monitored by TLC or HPLC using UV detection. After the complete disappearance of cinnamic acid ester the excess diamine is distilled off under vacuum.

This amidification can also be carried out under atmospheric pressure under blanket of nitrogen with an arrangement for selective condensation of the diamine and continuous removal of lower alcohol. The same reaction can be performed using cinnamic acid in place of cinnamic acid ester at temperatures up to 200° C. and pressures of 100 psi, keeping the same stoichiometry (1:1.2 to 3). The excess diamine serves as solvent for the reaction.

The bis-quaternaries (Formula I) of the present invention are synthesized as concentrated solutions by N-alkylating cinnamidoamines (Formula IV) with bifunctional alkylating agents having Formula V.

In another aspect this invention provides compositions containing quaternary ammonium compounds that are water-soluble, UV-absorbing and substantive to skin, hair and textile fibres. The hair care and skin care compositions containing compounds of Formula I can be solutions, dispersions or emulsions. The quaternary compounds of Formula I are soluble in water, alcohols, glycols, mixtures thereof, mixtures of alcohols and water and mixtures of glycols and water.

Lotions may be formed using compounds of Formula I, with or without one or more of the inert solvents like ethyl alcohol, isopropyl alcohol or propylene glycol, by combining with film forming polymers like proteins, polyvinyl pyrrolidone, polyvinyl alcohols and the like, film-forming starches and resins and the like.

Oil-in-water and water-in-oil emulsion can also be employed as vehicles to form lotions and creams. Conventional oil soluble UV-absorbing compounds like cinnamates, salicylates, p-aminobenzoates, benzophenones can be dissolved in oily phase of emulsion/lotions. The water-soluble sunscreens of the present invention are dissolved in an aqueous phase of the emulsion and combined with the oily phase using a suitable cationic emulsifier such as stearylkonium chloride.

Vegetable or mineral oils suitable for use as oil phase include mineral oil, petroleum, castor oil, sesame oil and the like. The quaternary ammonium compounds of the present invention are added to aqueous phase which is then subsequently emulsified with oily phase using an emulsifier like stearylkonium chloride or non-ionic emulsifiers like polysorbate-80, fatty alcohol ethoxylates and the like.

Perfumes, fragrances, anti-oxidants, preservatives, dyes colorants, insect repellents, fillers and suspended particulate matter, emollients, humectants, thickeners and the like may optionally be included in the sunscreen and tanning compositions of the present invention.

The sunscreen and tanning compositions of the present invention contain an effective amount of compounds of Formula I to prevent erythema. In general, an amount of about 0.5% to 10% w/w of the total composition is used.

Face powder compositions of the present invention contain compounds of Formula I in an effective amount of 0.1% w/w to 0.5% w/w.

The compositions containing compounds of Formula I may contain one or more of the other ingredients selected form cosmetic agents such as surfactants, other sunscreen chemicals, after sun treatment materials, emollients, humectants, perfumes, anti-perspirants, moisturisers, color cosmetic materials, herbal extracts, occlusive oils and essential oils.

The compositions of compound with Formula I provide hair protection from UV radiation in addition to good conditioning effect. The hair protecting preparations can be formulated in the form of creams, lotions, tonics or gels.

The compounds of the present invention may also be formulated as hair care product such as shampoos, cream rinses, hair conditioners, hair dressing preparations, hair relaxers, hair coloring products and the like, capable of protecting hair from UV-B radiation.

The rinse-off preparations like shampoos, face washes and bathing bars contain 0.5 to 8.0% w/w of compounds of Formula I. It may be noted that these quaternaries are compatible with usual anti-dandruff, anti-microbial agents like Zinc pyrithione, Irgasan, Pyroctone. Hence, these compounds of Formula I can be incorporated in anti-dandruff shampoos.

Despite their cationic nature, the compounds of Formula I are completely compatible with anionic surfactants like sodium lauryl ether sulphate. The water insolubility and cationic nature does not affect transparency of transparent shampoo. The shampoo formulation thus made has been shown to deposit the quaternary compounds on hair (Example III). The cream hair conditioner is an example of emulsion type with both water-soluble and water-insoluble sunscreens is given in Example IV.

Soap bars, both opaque and transparent I translucent can be formulated with compounds of UV-absorbing compounds of Formula I. In soap bars, the cinnamidoalkyl quaternary ammonium compounds can be incorporated from 0.5 to 10.0% w/w, more preferably from 1.0 to 2.0% w/w of total composition. It may be noted that the compounds of Formula I in the following combi-bar formulation are compatible with anionic surfactants (Example V).

For everyday use a sunscreen cream to protect the skin from both UV-A and UV-B radiation can be formulated as given in Example VI. The substantive UV absorbers, both water-insoluble and water-soluble (compounds of Formula I) can be conveniently incorporated at 2.0% each w/w of total composition. To cover UV-A range butyl methoxy dibenzoyl methane (Parsol 1789) is incorporated.

Furthermore, the compounds of Formula I of the present invention can be effectively incorporated into typical detergent powder and household cleaning product compositions to impart anti-fading effect to colored fabric through substantivity. Typical detergent and household cleaning product compositions in accordance with the present invention include one or more surfactants, selected from anionic, cationic, nonionic and amphoteric detergents, alone or in combination. A typical detergent powder has been shown to deposit cationic photofilters of the present invention on fabric (Example VII).

The hair and skin protecting and detergent and household cleaning compositions of the present invention are also formed by admixing, dissolving the compounds of Formula I into the desired cosmetically acceptable diluent and carrier. The preferred cosmetic compositions are solutions, dispersions or emulsions. The compositions contain an effective amount of one or more of UV-absorbing and conditioning compounds of the present invention to prevent erythema and darkening of skin due to solar damage.

In general, an amount of about 0.5% to about 10% w/w and preferably between 2.5 to 8.0% w/w of total cosmetic composition of compounds of Formula I are useful in personal hair and skin care products, sunscreens and tanning lotions. Typically, the ingredients are combined with mixing and heating if necessary until a uniform, homogeneous product is formed. With respect to the emulsion products of the present invention, the water-soluble and water-insoluble ingredients are mixed together separately and combined with suitable emulsifier, preferably a cationic emulsifier, to form an emulsion.

Finally, the substantive UV-B absorbers of the present invention are non-hydrolysable and contain the most widely used chromophore of cinnamido moiety for UV absorption. A representative substantive bis-quaternary compound of the present invention, $\beta,\beta'$-di (p-methoxy cinnamidopropyldimethylammonium chloride) ethyl ether, has molar extinction coefficient, $\epsilon$ of 42,000. It is non-irritant and non-mutagenic. High water-solubility coupled with substantivity of the compounds of the present invention, is very much desired in cosmetic formulations without an oily phase. Unlike the quaternary UV-absorbers of previous art that are described as water-dispersible/soluble, the bis-quaternary compounds of the present invention exhibit high water-solubility due to oxyethylene bridge between two UV-absorbing moieties.

EXAMPLES

The invention will now be illustrated with the help of examples, Examples I and II for process and Examples III to VII for compositions. The examples are by way of illustrations only and in no way restrict the scope of invention. Many changes and modifications can be made within the scope of the invention without departing with spirit thereof and the invention includes all such modifications. A few formula variations for the preparation of shampoo, cream hair conditioner, transparent bathing bar, sunscreen cream and detergent powder with compounds of Formula I are illustrated in Examples III, IV, V, VI and VII respectively.

Example I

Process for Preparation of $\beta,\beta'$-di(p-Methoxy Cinnamidopropyldimethylammonium Chloride) Ethyl Ether from Ethyl p-Methoxy Cinnamate The compound of Formula I wherein $R_1=OCH_3$, $R_2=H$, $R_3$, $R_4=CH_3$, n=3, m=1, X=Cl.

p-Methoxy cinnamidopropyldimethylamine was synthesised according to procedure described below.
a) Preparation of p-Methoxy Cinnamidopropyldimethylamine Ethyl p-methoxy cinnamate (206.0 g, 1.0 mole), N,N-dimethylpropylamine (306.0 g, 3.0 mole) and sodium methoxide (2.0 g) were charged in a pressure reactor. The air inside the reactor was flushed out by purging of nitrogen. The reaction mixture was then stirred at 180° C. (this generated pressure of 18 kg/cm$^2$) for 36 hours. The progress of reaction was monitored by disappearance of ethyl p-methoxy cinnamate on chromatography (TLC and HPLC). The TLC was performed on aluminium coated silica gel plates (Merck-60-F-254) and viewed with a UV lamp at 254 nm. HPLC was performed using reversed phase technique on a C-18 bonded (octadecyl silane) column and 60% aqueous methanol as mobile phase (1.0 ml/min) and detection at 280 nm. The excess amine was removed under vacuum. The golden yellow solid (263.0 g) thus obtained had amine value of 245. Molar extinction coefficient, $\epsilon$, in methanol was found to be 24,224 at 290 nm.

IR in dichloromethane showed carbonyl stretching of amide at 1660 cm$^{-1}$ and NH stretching at 3300 cm$^{-1}$.

$^1$H NMR (300 MHz, CDCl$_3$): $\delta$1.73 (p, 2H, J=6.6 Hz), 2.26 (s, 6H), 2.42 (t, 2H, J=6.6 Hz), 3.45 (q, 2H, J=6.0 Hz), 3.81 (s, 3H), 6.27 (d, 1H, J=15.6 Hz), 6.86 (d, 2H, J=8.7 Hz), 7.43 (d, 2H, J=8.7 Hz), 7.53 (d, 1H, J=15.6 Hz).

b) Preparation of $\beta,\beta'$-di(p-Methoxy Cinnamidopropyldimethylammonium Chloride) Ethyl Ether (Formula I):

p-Methoxy cinnamidopropyldimethylamine (263.0 g, 1.0 mole) and bis-(2-dichloroethyl)ether (71.5 g, 0.5 mole) and deionised water (334.5 ml) were charged in a pressure reactor. The air inside was flushed out by purging nitrogen. The reaction mixture was then stirred at 115° C. (pressure 3 kg/cm$^2$) for 36 hours. The progress of the reaction was followed by analysing the chloride content. The reaction yielded 669.0 g of product as light amber colored liquid with slight cinnamom like odor, pH 7.5, chloride content of 5.2% and solids 50%. Removal of water afforded off-white, sticky, hygroscopic solid that was highly water-soluble (>50%).

The molar extinction coefficient, $\epsilon$ in aqueous solution at 292 nm $\lambda$max was found to be 42,729.

$^1$H NMR (300 MHz, D$_2$O): $\delta$ 1.98 (m, 4H), 3.11 (s, 12H), 3.29 (t, 4H, J=6.3 Hz), 3.39 (m, 4H), 3.60 (improperly resolved triplet, 4H), 3.71 (s, 6H), 3.94 (improperly resolved triplet, 4H), 6.27 (d, 2H, J=15.6 Hz), 6.84 (d, 4H, J=8.7 Hz), 7.29 (d, 2H, J=15.9 Hz), 7.38 (d, 4H, J=9.0 Hz).

Example II

Process for preparation of $\beta,\beta'$-di(p-Methoxy Cinnamidopropyldimethylammonium Chloride) Ethyl Ether from p-Methoxy Cinnamoyl Chloride a) Preparation of p-Methoxy Cinnamoyl Chloride:

To a stirred suspension of p-methoxy cinnamic acid (178.0 g, 1.0 mole) in dichloromethane (500 ml), thionyl chloride (238.0 g, 2.0 moles) was added slowly and the reaction mass was heated at 45° C. for 3 hours. The excess of thionyl chloride was removed under vacuum and the p-methoxy cinnamoyl chloride was distilled (145° C./0.2 mm) in 85% yield as colourless solid with m.p. 50° C. (Literature m.p. 50° C., Dictionary of Organic Compounds, Chapmann and Hall, 1994).

b) Preparation of p-Methoxy Cinnamidopropyldimethylamine:

To a stirred solution of N,N-dimethylpropyldiamine (102.0 g, 1.0 mole) in dichloromethane (500 ml), solution of p-methoxy cinnamoyl chloride (196.0 g, 1.0 mole) in dichloromethane from step (a) was slowly added and the reaction was continued at room temperature for 2 hours. The reaction mixture in dichloromethane was washed with aqueous sodium hydroxide (200 ml, 20.0%). The organic layer was dried over anhydrous sodium sulphate. The removal of solvent using a rotary evaporator afforded the p-methoxy cinnamidopropyldimethylamine (235.0 g) as colourless solid, m.p. 80° C. Reversed phase HPLC showed it to be 98% pure with amine value 217.

The NMR, IR and HPLC data matched with the data for the compound obtained in Example I.

c) Preparation of β,β'-di(p-Methoxy Cinnamidopropyldimethylammonium Chloride) Ethyl Ether (Formula I):

A mixture of p-methoxy cinnamidopropyldimethylamine (264.0 g, 1.0 mole) and bis-(2-dichloroethyl)ether (71.5 g, 0.5 mole) and isopropanol (334.5 ml) was stirred under nitrogen in an open vessel at 85° C. for 36 hours.

The progress of the reaction was followed by analysing the chloride content. The reaction yielded 669.0 g of product as light amber colored liquid, chloride content of 5.2% and solids 50%.

A small sample was then dried in oven at 105° C. to yield the bis-quaternary as pale yellow solid, the PMR, molar extinction coefficient, surface tension of which were found to be identical with the one obtained from the experiment described in step (b) of Example I.

Example III

Preparation of Transparent Shampoo

A shampoo composition containing β,β'-di(p-methoxy cinnamidopropyldimethylammonium chloride) ethyl ether of Example I was prepared in accordance with the optimum formulation given below. Acceptable formula variations for the preparation of such shampoo are also illustrated.

| Ingredient | Range % (w/w) | Preferred % (w/w) | Optimum % (w/w) |
| --- | --- | --- | --- |
| SLES-2 (30%) | 40–60 | 45–60 | 50.00 |
| CAPB (30%) | 1–10 | 2–10 | 8.00 |
| β,β'-di(p-methoxy cinnamidopropyl dimethylammonium chloride) ethyl ether | 0.5–10 | 2–5 | 2.00 |
| Galsilk | 3–10 | 4–6 | 5.00 |
| Chelating agents/sodium chloride/preservatives/colour and fragrances | Quantity sufficient | | |
| Deionised water | Quantity sufficient to make 100% | | |

A clear shampoo was formulated using β,β'-di(p-methoxy cinnamidopropyldimethylammonium chloride) ethyl ether prepared as in Example I. The other active ingredients, SLES-2, Sodium lauryl ether sulphate, an anionic surfactant, 30% aqueous solution, CAPB, Cocoamidopropyl betaine, an amphoteric surfactant, 30% aqueous solution and Galsilk, Polyquaternium-7 were obtained from Galaxy Surfactants Ltd., Mumbai, India, Methyl paraben and propyl paraben were obtained from Gayatri Laboratories, Mumbai, India. Approved fragrances and colors were obtained from S. H. Kelkar & Co., Mumbai, India and Koel Colors Pvt. Ltd., Mumbai, India respectively.

The transparent shampoo was prepared as follows:

The major ingredients were mixed with heating to 50° C. until a uniform homogenous mixture was formed. The resulting mixture was then cooled to room temperature with continuous stirring. The required chelating agent, colour, perfume were added. The viscosity was adjusted to 2500 cps with sodium chloride.

The β,β'-di(p-methoxy cinnamidopropyldimethylammonium chloride) ethyl ether was found to be completely compatible with anionic surfactant. The substantivity experiment was performed as described under;

Virgin hair (5.0 g) were washed with 10% SLES solution and rinsed with plain water. The tresses were treated for exactly 5.0 minutes with clear shampoo (containing 2% β,β'-di (p-methoxy cinnamidopropyldimethylammonium chloride) ethyl ether) as described in Example I that was diluted five times with water. After the treatment the tresses were washed thoroughly with copious amount of water. The adsorbed quaternary was extracted from the hair surface by immersing each tress in isopropanol at 65° C. for 30 minutes. A known volume of this isopropanol/quaternary ammonium salt mixture was analysed by UV-spectroscopy to determine its absorption intensity.

The substantivity was found to be 22 mg/100 g of hair.

Example IV

Preparation of Cream Hair Conditioner

A cream hair conditioner containing β,β'-di(p-methoxy cinnamidopropyldimethylammonium chloride) ethyl ether of Example I was prepared in accordance with the optimum formulation given below. Acceptable formula variations for the preparation of such cream hair conditioner are also illustrated.

| Ingredient | Range % (w/w) | Preferred % (w/w) | Optimum % (w/w) |
| --- | --- | --- | --- |
| β,β'-di(p-methoxy cinnamidopropyl dimethylammonium chloride) ethyl ether | 0.5–5 | 1–3 | 2.0 |
| Cocoamidopropyl betaine | 1–6 | 0.5–2 | 0.5 |
| Cetyl trimethyl ammonium chloride | 1–15 | 4–10 | 4.5 |
| Cetostearyl alcohol | 1–15 | 5–10 | 5.5 |
| Lanoline | 0.5–1.0 | 1–5 | 1.5 |
| Isopropyl myristate | 0.5–5 | 1–3 | 1.0 |
| Chelating agents/preservatives/fragrance | Quantity sufficient | | |
| Deionised water | Quantity sufficient to make 100% | | |

Cetyltrimethylammonium chloride was obtained from Flame Pharmaceuticals Pvt. Ltd., Mumbai, India, Isopropyl myristate was obtained from Anusynth Chemical Industries, Mumbai, India, Lanoline was obtained from Rolex Lanoline Products Ltd., Mumbai, India. Phenoxyethanol was obtained from Galaxy Surfactants Ltd., Mumbai, India.

The cream hair conditioner was prepared as follows

Aqueous phase containing cetyltrimethylammonium chloride, cocoamidopropyl betaine, β,β'-di(p-methoxy cinnamidopropyldimethylammonium chloride) ethyl ether and water were stirred together at 70° C. Oily phase comprising cetostearyl alcohol, isopropyl myristate, lanoline and preservatives was maintained at 70° C. under stirring. The oily phase is slowly added to the stirred aqueous phase at 70° C. and the whole mixture was cooled under vigorous stirring to 40° C. Perfume and other additives were added and continued cooling under stirring to get good cream.

Example V

Preparation of Transparent Bathing Bar

A transparent bathing bar containing β,β'-di(p-methoxy cinnamidopropyldimethylammonium chloride) ethyl ether of Example II was prepared in accordance with the optimum formulation given below. Acceptable formula variations for the preparation of such transparent bathing bar are also illustrated.

| Ingredient | Range % (w/w) | Preferred % (w/w) | Optimum % (w/w) |
| --- | --- | --- | --- |
| SLES (30%) | 10–50 | 20–35 | 28 |
| CAPB (30%) | 5–30 | 10–20 | 16 |
| Sodium cocoate | 5–20 | 10–15 | 9.0 |
| Sodium stearate | 15–70 | 15–20 | 13.8 |
| Propylene Glycol | 10–30 | 10–25 | 20 |
| Sorbitol (70%) | 4–15 | 8–10 | 8.0 |
| β,β'-di(p-methoxy cinnamidopropyl dimethylammonium chloride) ethyl ether | 0.5–10 | 1.0–5.0 | 2.0 |
| Chelating agent/colour and fragrance | Quantity sufficient | | |
| Deionised water | Quantity sufficient to make 100% | | |

The transparent bathing bar was prepared as follows:

All ingredients were heated together under stirring to 70° C. till the reaction mass became homogenous and transparent. The reaction mass was cooled to 40° C. and the required amounts of chelating agents, perfume and colour were added. The molten mass was cast in moulds of desired shape to yield transparent bathing bar. It could be easily seen that the transparency of bathing bar was unaffected proving the total compatibility of β,β'-di (p-methoxy cinnamidopropyl dimethylammonium chloride) ethyl ether with anionic surfactant. The transparent bar thus made was evaluated as per the procedure described in Example III and the substantivity was found to be 20 mg /100 g of hair.

Example VI

Preparation of Sunscreen Cream

A sunscreen cream for every day use containing β,β'-di (p-methoxy cinnamidopropyl dimethylammonium chloride) ethyl ether of Example I was prepared in accordance with the optimum formulation given below. Acceptable formula variations for the preparation of such sunscreen cream are also illustrated.

| Ingredient | Range % (w/w) | Preferred % (w/w) | Optimum % (w/w) |
| --- | --- | --- | --- |
| β,β'-di(p-methoxy cinnamidopropyl dimethylammonium chloride) ethyl ether | 1–10 | 1–5 | 2.0 |
| Octyl methoxy cinnamate | 1–10 | 1–5 | 2.0 |
| Parsol-1789 (UV-A filter) | 1–5 | 1–3 | 1.0 |
| Polysorbate-80 (Tween-80) | 1–12 | 3–7 | 5.0 |
| Lauryl alcohol ethoxylate - 9 EO | 1–12 | 3–7 | 5.0 |
| Liquid paraffin oil | 1–12 | 3–7 | 5.0 |
| Isopropyl myristate | 1–12 | 3–7 | 5.0 |
| Ethylene glycol monostearate | 1–12 | 3–7 | 5.0 |
| Glyceryl monostearate | 1–12 | 3–7 | 5.0 |
| Cetostearyl alcohol | 1–12 | 3–7 | 5.0 |
| Dimethicone copolyol | 1–10 | 2–3 | 2.0 |
| Vitamin E acetate | 0.5–5 | 1–3 | 0.5 |
| Niacinamide | 0.5–5 | 1–3 | 1.0 |
| Hydroquinone | 0.5–3 | 1–2 | 1.0 |
| Sodium sulphite | 0.1–1 | 0.1–0.5 | 0.2 |
| Preservatives/fragrance | Quantity sufficient | | |
| Deionised water | Quantity sufficient to make 100% | | |

Parsol-1789 was procured from Givaudan, Roure, USA. Tween-80, Niacinamide and Vitamin E acetate were obtained from S. D. Fine Chem., Mumbai, India. Lauryl alcohol ethoxylate, ethylene glycol monostearate, glyceryl monostearate and octyl methoxy cinnamate were obtained from Galaxy Surfactants Ltd., Mumbai, India. Dimethicone copolyol (SF 11 88A) was obtained from General Electric, Bangalore, India.

The sunscreen cream was prepared as follows:

Aqueous phase containing β,β'-di(p-methoxy cinnamidopropyldimethylammonium chloride) ethyl ether, Tween-80, lauryl alcohol ethoxylate-9 EO, sodium sulphite, dimethicone copolyol and water was stirred at 70° C. The oily phase comprising of octyl methoxy cinnamate, isopropyl myristate, paraffin oil, glyceryl monostearate, ethylene glycol monostearate, Vitamin E acetate, cetostearyl alcohol, niacinamide, hydroquinone and the preservatives was heated under stirring to 70° C. The oily phase is then added to the vigorously stirred aqueous phase and cooled under stirring to 40° C. At this stage fragrances were added and cooled under stirring to room temperature to get a good shiny cream.

Example VII

Preparation of Detergent Powder

A detergent powder containing β,β'-di(p-methoxy cinnamidopropyldimethylammonium chloride) ethyl ether of Example I was prepared in accordance with the optimum formulation given below. Acceptable formula variations for the preparation of such detergent powder are also illustrated.

| Ingredient | Range % (w/w) | Preferred % (w/w) | Optimum % (w/w) |
| --- | --- | --- | --- |
| Soda ash | 20–50 | 20–30 | 20 |
| Sodium tripolyphosphate | 1–30 | 15–25 | 25 |
| Sodium alkyl benzene sulphonate | 10–50 | 10–30 | 20 |
| Sodium chloride | 1–45 | 5–15 | 5.0 |
| Sodium sulphate | 1–40 | 10–20 | 20 |
| β,β'-di(p-methoxy cinnamidopropyl dimethylammonium chloride) ethyl ether | 0.5–10 | 2–4 | 2.0 |
| Sodium carboxy methyl cellulose | 0.5–5 | 1–2 | 1.0 |
| Sodium silicate | 1–5 | 1–2 | 2.0 |
| Chelating agent/colour and fragrances | Quantity sufficient | | |

Linear alkyl benzene sulphonic acid was obtained from Albright and Wilson Chemicals (India) Ltd., Mumbai, India.

The detergent powder was prepared as follows:

To a stirred mixture of soda ash, sodium tripolyphosphate, sodium chloride and sodium sulphate, linear alkyl benzene sulphonic acid was slowly added. The mixture was then cooled to room temperature. Other active ingredients including sodium carboxy methyl cellulose, sodium silicate and β,β'-di(p-methoxy cinnamidopropyldimethylammonium chloride) ethyl ether were then added to this mixture along with the other additives like nonionic surfactant, bleaching agent, optical brightener, chelating agent, colour and perfume and stirring was continued to get uniform detergent powder.

The detergent thus made was evaluated for the deposition of quaternary on cotton fabric (substantivity) as per the principles described in Example III and was found to be 21 mg/100 g of cotton fabric.

What is claimed is:

1. A water-soluble quaternary ammonium salt of bis-cinnamidoalkylamine of Formula I (I)

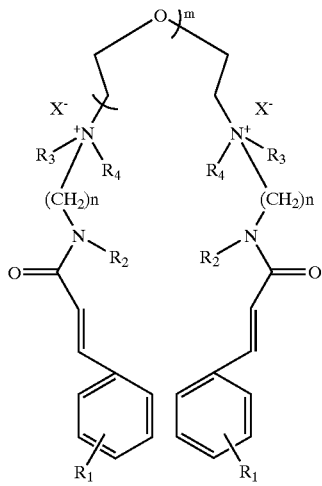

wherein $R_1$ represents up to four substituents, same or different, selected from H, halo, —OH, —$NH_2$, —$NO_2$, —$OCH_3$, —$N(CH_3)_2$, alkyl groups containing up to 6 carbon atoms, alkoxy groups containing up to 6 carbon atoms, alkylamino or N,N-dialkylamino groups containing up to 6 carbon atoms;

$R_2$ is selected from hydrogen, alkyl group containing up to 6 carbon atoms;

$R_3$ and $R_4$ are independently selected from benzyl, alkyl group containing up to 6 carbon atoms, n is an integer from 1 to 6; m is an integer from 1 to 10;

$X^-$ is a counter anion of quaternary centres selected from halides including chloride, bromide, iodide and methane sulphonate and its derivatives such as trifluoro methane sulphonate, benzene sulphonates including its p-bromo, nitro and methyl derivative.

2. A quaternary salt of claim 1, wherein the salt is β,β'-di(p-methoxy cinnamidopropyldimethylammonium chloride) ethyl ether, wherein, $R_1$=para —$OCH_3$, $R_2$=—H, $R_3$=$R_4$=—$CH_3$, $X^-$=$Cl^-$, m=1 and n=3.

3. A process of making a water-soluble quaternary ammonium salt of bis-cinnamidoalkylamine of Formula I (I)

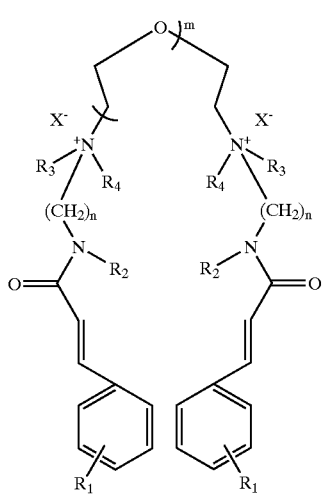

wherein $R_1$ represents up to four substituents, same or different, selected from H, halo, —OH, —$NH_2$, —$NO_2$, —$OCH_3$, —$N(CH_3)_2$, alkyl groups containing up to 6 carbon atoms, alkoxy groups containing up to 6 carbon atoms, alkylamino or N,N-dialkylamino groups containing up to 6 carbon atoms;

$R_2$ is selected from hydrogen, alkyl group containing up to 6 carbon atoms;

$R_3$ and $R_4$ are independently selected from benzyl, alkyl group containing up to 6 carbon atoms;

n is an integer from 1 to 6; m is an integer of from 1 to 10; and $X^-$ is a counter anion of quaternary centres selected from halides including chlorine, bromide, iodide and methane sulphonate and its derivatives including trifluoro methane sulphonate, benzene sulphonates including its p-bromo, nitro and methyl derivative;

wherein, a compound of Formula II is first reacted with a compound of Formula III to produce an intermediate compound of Formula IV which is quaternized with a compound of Formula V to provide the compound of Formula I (II)

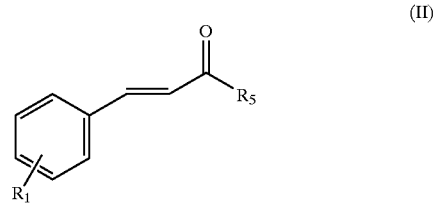

(III)

(IV)

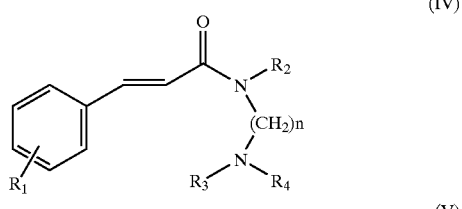

(V)

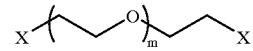

wherein in all the formulae, $R_1$, $R_2$, $R_3$, $R_4$, m, n and $X^-$ have the same meaning as Formula I, and $R_5$ of Formula II is selected from —OH, $Cl^-$ or —$O(CH_2)_pCH_3$ with p=0 to 3.

4. A composition comprising a bis-cinnamidoalkylamine cationic salt of claim 1 and one or more of other cosmetic ingredients that are selected from cosmetic agents such as aqueous and oily moisturisers, film forming agents, emulsifiers, thickening agents, skin and hair conditioning agents, humectants, vegetable oils, surfactants, emollients and rheological modifiers.

5. The composition of claim 4, wherein other active ingredients comprise of detergents that are selected from the group consisting of anionic detergents, cationic detergents, non-ionic detergents and amphoteric detergents.

6. The composition of claim 4, wherein said bis-cinnamidoalkylamine quaternary salt is present in an amount in the range from about 0.5% to about 10.0% w/w of said composition.

7. The composition of claim 4, wherein the other ingredients are chosen to give a shampoo formulation.

8. The composition of claim 4, wherein the other ingredients are chosen to give a hair conditioner formulation.

9. The composition of claim 4, wherein the other ingredients are chosen to give a bathing bar formulation.

10. The composition of claim 4, wherein the other ingredients are chosen to give a sunscreen cream formulation.

11. The composition of claim 4, wherein the other ingredients are chosen to give a detergent powder formulation.

12. The water-soluble quaternary ammonium salt of bis-cinnamidoalkylamine of claim 1, wherein $R_1$ is —$OCH_3$, $R_2$ is hydrogen, $R_3$ is an alkyl group containing up to 6 carbon atoms, $R_4$ is an alkyl group containing up to 6 carbon atoms, $X^-$ is $Cl^-$, m is from 2 to 6, and n is 3.

13. The water-soluble quaternary ammonium salt of bis-cinnamidoalkylamine of claim 1, wherein the compound of Formula I is β,β'-di (p-methoxy cinnamidopropyldimethyl ammonium chloride)ethyl ether.

14. The process of claim 3, wherein $R_1$ is —$OCH_3$, $R_2$ is hydrogen, $R_3$ is an alkyl group containing up to 6 carbon atoms, $R_4$ is an alkyl group containing up to 6 carbon atoms, $X^-$ is $Cl^-$, m is from 2 to 6, and n is 3.

15. The process of claim 3, wherein the compound of Formula I is β,β'-di (p-methoxy cinnamidopropyldimethyl ammonium chloride)ethyl ether, the compound of Formula II is p-methoxy ethyl cinnamate, the compound of Formula III is N,N-dimethylpropyldiamine, and the intermediate compound of Formula IV is p-methoxy cinnamidopropyldimethyl amine.

* * * * *